United States Patent [19]

Albright

[11] Patent Number: 5,300,288
[45] Date of Patent: Apr. 5, 1994

[54] COMPOSITION AND METHOD FOR CONTROLLING CHOLESTEROL

[75] Inventor: Robert L. Albright, Churchville, Pa.

[73] Assignee: Rohm and Haas Company, Philadelphia, Pa.

[21] Appl. No.: 681,032

[22] Filed: Apr. 5, 1991

[51] Int. Cl.$^5$ .......................................... A61K 31/765
[52] U.S. Cl. ............................... 424/78.08; 526/307; 526/307.1
[58] Field of Search ................. 424/81, 78, 78.08; 526/307, 307.1

[56] References Cited
U.S. PATENT DOCUMENTS 3,733,460  5/1973  Freeville et al. ...................... 424/81
4,211,765  7/1980  Johnson et al. ....................... 424/78
4,911,917  3/1990  Kuhrts ................................. 424/682

*Primary Examiner*—Thurman K. Page
*Assistant Examiner*—P. Kulkosky
*Attorney, Agent, or Firm*—John E. Taylor, III

[57] ABSTRACT

A nontoxic polymer comprising a backbone having a pendant groups which have sites which are capable of forming ionic bonds and sites capable of forming hydrogen bonds with respective receptive sites on the anions of conjugate acids formed by the reaction of bile acids with glycine and of bile acids with taurine, preferred polymers including polymeric amides, and pharmaceutical compositions containing the same for treatment of hypercholesterolemia.

45 Claims, No Drawings

COMPOSITION AND METHOD FOR CONTROLLING CHOLESTEROL

FIELD OF THE INVENTION

This invention is in the field of therapeutic compositions and methods for controlling blood cholesterol. More specifically, this invention relates to chemical compositions which sequester the bile acids in the digestive tract and which prevent reabsorption of the bile acids into the bloodstream, and to the method of using such compositions in the treatment of hyperchloesterolemia.

Direct relationships are known to exist between blood serum cholesterol level, incidence of atherosclerosis, and the risk of coronary heart disease. Over the years, several approaches have been taken toward controlling the chloesterol level in mammalian blood. Changes in the diet are capable of lowering the cholesterol level somewhat when cholesterol-producing foods are minimized or eliminated from the diet. However, quite apart from dietary intake, cholesterol is produced in the liver, and the most advanced treatment for hypercholesterolemia involves the administration of a drug which affects this process.

A drug which is effective in this regard is lovastatin, the common name for a metabolite produced by a certain fungus, as disclosed in U.S. Pat. No. 4,231,938. (Lovastatin is sold by Merck and Co. under the trademark MEVACOR ®.) Lovastatin, which is systemic, appears to disrupt the biosynthesis of cholesterol in the liver, where about 70% to 80% of body cholesterol is produced. The synthesis of cholesterol has been shown to involve a series of enzyme-catalyzed process steps starting from acetate. Lovastatin interrupts the fifth step of that process by inhibiting HMG coenzyme A reductase. With synthesis in the liver inhibited, the liver cells must take cholesterol from the bloodstream, and they do so by increasing their production of cell surface receptors for LDL-cholesterol. Lovastatin is capable of lowering the blood serum cholesterol level by about 30-40%.

Even greater reductions of blood serum cholesterol level would be desirable for the treatment of hypercholesterolemia. Accordingly, the use of lovastatin alone provides only limited benefits.

In the liver, cholesterol is not only produced, it is also consumed in the production of bile acids. The bile acids are steroidal compounds which are transported as the conjugate acids of cholic and deoxycholic acid with glycine and taurine. Unless indicated otherwise, the term "bile acids" is used herein for convenience in referring to such conjugate acids. The bile acids are stored in the gallbladder and introduced into the duodenum to aid with the digestion of fats in the intestine. After such use, the bile acids are absorbed into the intestinal bloodstream and returned to the liver. Removal of bile acids in the digestive tract in turn lowers the concentration of cholesterol in the blood by forcing the liver to obtain more cholesterol from the bloodstream for bile acid production. This invention relates to the provision of materials which are capable of combining with bile acids in the digestive tract and placing them in a form such that they are excreted from the body without reabsorption.

Reported Developments

Two materials which are known to be effective in lowering blood cholesterol levels by acting on bile acids in the digestive tract are cholestyramine and cholestipol.

Cholestyramine is disclosed in U.S. Pat. No. 3,383,281, and its commercial use predates the introduction of lovastatin by a number of years. Cholestyramine is a polystyrene resin which is lightly crosslinked with divinylbenzene and functionalized with quaternary ammonium groups. Another resin which operates in a fashion similar to cholestyramine is cholestipol, as described in U.S. Pat. No. 3,692,895. Cholestipol is a crosslinked polymeric material derived from the condensation of a polyamine with epichlorohydrin.

Cholestyramine and cholestipol perform in the digestive tract as a water-insoluble anionic exchange resin to sequester bile acid anions and take them out of solution. The sequestered bile acids are eliminated from the body along with fecal matter. The use of such resins can lower blood cholesterol levels by 25-30%. However, ground ion exchange resins such as cholestryamine and cholestipol are gritty and unpleasant to swallow. Another disadvantage associated with the use of these materials is that they are inefficient. Studies have shown that only about 5% of the available binding sites in cholestyramine are actually taken up with bile acids. Thus, therapeutic daily doses of the resins are of necessity undesirably large, that is, 12-15 grams/day. In addition, the use of cholestyramine and cholestipol is typically accompanied by unpleasant side effects, such as bloating, gas, constipation, and diarrhea.

The present invention is directed to providing improved therapeutic compositions for sequestering bile acids in the digestive tract. In performing this function, the invention is similar to cholestyramine and cholestipol, but it performs with greater efficacy.

OBJECTS OF THE INVENTION

One object of this invention is to provide a bile acid sequestrant which is more effective than the resins currently available. As a corollary, another objective of this invention is to provide a bile acid sequestrant which can be employed at lower dosages than cholestyramine or cholestipol. Yet another objective is to provide a sequestrant which is not unpleasant to ingest, including sequestrants which are water soluble.

SUMMARY OF THE INVENTION

The above and other objectives are attained by the provision of polymers which, in contrast to the resins of the prior art, comprise a backbone to which is attached pendant groups having sites capable of forming ionic bonds and sites which are capable of forming hydrogen bonds with respective receptive sites on the anions of conjugate acids formed by the reactions of bile acids with glycine and by bile acids with taurine. Polymers which we have found to have these properties are those having the following structure:

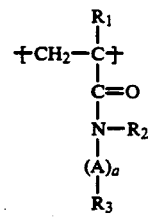

Formula 1 wherein

A is selected independently from
an oxyalkyl group —(CHR$_4$)$_b$—O—,
a thioalkyl group —(CHR$_5$)$_c$—S or
an aminoalkyl group —(CHR$_6$)$_d$—NR$_7$—,
the alkyl being attached to the amide nitrogen;

a is an integer between 0 and about 10;

b, c, and d are independently integers between 1 and about 10;

R$_1$ is hydrogen or a C$_1$-C$_8$ hydrocarbon group,

R$_2$ and R$_7$ are independently hydrogen, hydrocarbon groups or heteroatom-containing hydrocarbon groups, R$_4$, R$_5$, and R$_6$ are independently hydrogen, hydrocarbon groups or heteroatom-containing hydrocarbon groups; and R$_3$ is

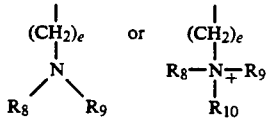

wherein e is an integer from 1 to 6, and

R$_8$, R$_9$ and R$_{10}$ are independently hydrogen, hydrocarbon groups of heteroatom-containing hydrocarbon groups.

These polymers also have a molecular size distribution with a mode of about 80,000 daltons or greater, more preferably about 250,000 daltons or greater, with less than about 5 wt. % of the polymers having a size of about 50,000 daltons or less. Also, a polymeric composition for use in treating humans in accordance with the present invention contains no more than about 1000 ppm by weight of the monomer from which the polymer is made, and more preferably, smaller amounts of the monomer, as described below.

We have also discovered a method for removing bile acids from the digestive tract of a host and reducing the blood cholesterol concentration thereof comprising the ingestion by the host of a nontoxic composition comprising one or more of the polymers of Formula 1 in an amount effective to remove bile acids from the digestive tract of the host.

DETAILED DESCRIPTION OF THE INVENTION

Compared to compounds of the prior art, such as cholestyramine and cholestipol, which function exclusively by ionic bonding, polymers of the present invention are significantly more efficient in that they are capable of sequestering substantially larger amounts of bile acids based on dose weight of the polymer. Test results reported hereinbelow show that polymers of the present invention are more efficient at a given dosage weight than the prior-art compounds mentioned above in lowering blood cholesterol levels.

By way of explanation, species of polymer within the scope of the present invention can be described as having a flexible backbone made up of monomeric units, at least some of which have bonded thereto flexible, highly mobile, chains which, for discussion purposes, may be regarded as tentacles which contain atoms or oligomeric groups of atoms that are capable of forming both hydrogen and ionic bonds to bile acids or anions thereof. Exemplary polymers may be represented diagrammatically as follows:

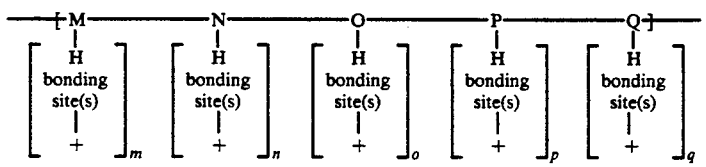

where the individual M to Q units may be the same or different monomeric units, with some or all of such units containing tentacles with bonding sites, that is, m to q may be 0 or 1.

Further, the hydroxyl groups at positions 3 and 12, and in some cases 7, on the steroid ring system of the bile acid molecules are all axial, projecting from the same side or face of the steroid ring structure. Thus, these hydroxyl groups are quite readily accessible (receptive) to form hydrogen bonds to appropriate groups on the tentacles.

The above diagrammatic representation is merely illustrative. For example, the tentacles can include additional hydrogen bonding site(s) and in positions, relative to the ionic bonding sites, which are different from those shown in the diagrammatic representation. Also, more than one ionic bonding site can be present on a tentacle. As indicated by the diagrammatic representation, the present invention includes within its scope resins in which fewer than all of the monomeric units can have attached thereto tentacles, and resins in which the monomeric units and/or the tentacles can be different, for example, as would be the case for resins which are copolymers, including copolymers of two or more monomers.

As stated above, the preferred polymers of the present invention are those which have a molecular size distribution with a mode of at least about 80,000 daltons, more preferably at least about 250,000 daltons, with less than about 5 wt. % of the polymers having a size of about 50,000 daltons or less. Also, a polymeric composition for use in treating humans in accordance with the present invention contains no more than about 1000 ppm by weight of the monomer from which the polymer is made, and more preferably, smaller amounts of the monomer, as described below. A preferred class of polymers for use in the practice of the present invention comprises polymeric amides, preferably polymeric amides which are water soluble or colloidal dispersions, with the water soluble polymers being more preferred.

Another aspect of the present invention comprises pharmaceutical compositions for use in treating hypercholesterolemia in mammals and comprising nontoxic, anionic ion exchange resins which contain both hydrogen bonding sites and ionic bonding sites for bonding respectively to hydroxyl groups which are present in molecules of conjugate acids formed by the reactions of bile acids with glycine and of bile acids with taurine and to anions thereof.

Still another aspect of the present invention comprises a composition which is effective in reducing the concentration of cholesterol in the blood of a host comprising non-toxic polymers of the type referred to above in admixture with a material which inhibits the synthesis of cholesterol in the liver of the host, for example, lovastatin. As used herein, the term "host" means a living vertebrate animal.

In addition to being highly efficient in sequestering bile acids in the digestive tract and in lowering the concentration of cholesterol in the blood, there are other advantages which flow from the use of polymers of the present invention. For example, species of polymers of the invention are available in palatable form and their use is not accompanied by the numerous adverse side effects which are encountered in the use of the above prior-art polymers.

As mentioned above, bile acid molecules have hydroxyl groups which are receptive sites for the formation of hydrogen bonds. In addition, bile acid molecules have groups which are capable of forming ionic bonds. The carboxylic acid group from glycocholic acid and from glycodeoxycholic acid is capable of ionizing leaving the molecule with a negatively-charged carboxylate group (COO—). With respect to taurocholic acid and taurodeoxycholic acid, each of these acids has a —SO₃H group which is capable of ionizing to form a negatively charged sulfonate group (SO₃—) attached to the molecule.

The polymers of the present invention include pendant groups which have a first site(s) capable of forming hydrogen bonds with the aforementioned receptive hydroxyl groups of the bile acid molecules and a second site(s) capable of forming ionic bonds with the negatively charged carboxylate and sulfonate groups of the bile acid molecules. Particularly good results have been achieved by the use of polymers which are linear.

As it refers to $R_2$ and $R_4$ through $R_{10}$ in the description of Formula 1 and in the claims, the term "hydrocarbon group" means an aromatic group or an aliphatic group which contains 1 to about 20 carbon atoms and is linear, branched or cyclic in form. Examples of such groups are alkyl groups, cycloalkyl groups, aryl groups, alkaryl groups and aralkyl groups. For purposes of this invention, alkyl groups include straight or branched chains of between 1 and about 20 carbon atoms, with alkyl groups containing 1 to about 6 carbon atoms being preferred and termed "lower" alkyl groups; specific examples include methyl, ethyl, n-propyl, isopropyl, n-butyl, t-butyl and n-hexyl. For purposes of this invention, cycloalkyl groups include cyclic and bicyclic rings of 3 to about 10 carbon atoms; rings of no greater than about 6 carbon atoms are preferred and are termed "lower" cycloalkyl groups; specific examples include cyclopentyl and cyclohexyl. For purposes of this invention, aryl groups include aromatic hydrocarbons, such as benzene; alkyl-substituted aromatic hydrocarbons (i.e., alkaryl), such as toluene; aryl-substituted alkyl hydrocarbons (i.e., aralkyl), such as benzyl; aryl-substituted aromatic hydrocarbons, such as biphenyl; as well as condensed ring aromatic hydrocarbons, such as naphthalene, anthracene, and phenanthrene, and alkylated derivatives thereof. The term "heteroatom-containing hydrocarbon group", as used herein, refers to a hydrocarbon group, as described above, which also contains from one to five heteroatoms selected from the group consisting of nitrogen, oxygen or sulfur. The heteroatom(s) can be present in the heteroatom-containing hydrocarbon group as a linking atom in a chain of atoms or as a substituent attached to an atom of the chain; thus the heteroatom may be present as, for example, an amino group (primary, secondary or tertiary), a hydroxyl group, an ether group, or a thio group.

The polymeric amides described above are polymers which have a backbone to which are attached amide groups having pendant tentacles which emanate from the amide nitrogen, the tentacles containing an ionizable amino group. Such an amino group is capable of forming an ionic bond with the negatively charged carboxylate and/or sulfonate group of a bile acid molecule. Also, when "a" of Formula 1, and of the corresponding formula in the claims, is other than zero, the tentacles carry polarizable oxygen, sulfur or nitrogen-containing groups "A" which are capable of forming hydrogen bonds with the axial hydroxyl groups of the bile acid molecules.

The polymeric amides can include "A" groups which are the same, or a mixture of two or three of the oxygen, sulfur, or nitrogen-containing groups described above. The preferred "A" groups are made up of oxyalkyl, thioalkyl, or aminoalkyl groups, with the alkyl group being a lower alkyl group.

The radical $R_1$ in Formula 1 and in the corresponding formula in the claims can be hydrogen or a $C_1$–$C_8$ hydrocarbon group; it is preferably hydrogen or alkyl, especially lower alkyl or hydrogen, and more preferably methyl or hydrogen. Polymeric amide backbones constructed of acrylamide or methacrylamide monomer units are also attractive because these monomers are readily available. The term "$C_1$–$C_8$ hydrocarbon group" means a linear or branched aliphatic hydrocarbon, an aromatic hydrocarbon, an alkaryl or an aralkyl hydrocarbon having from one to eight carbon atoms.

Similarly, the radical $R_2$ can also be hydrogen, a hydrocarbon group or a heteroatom-containing hydrocarbon group, as they are described above; the polymeric amides in which $R_2$ is hydrogen are preferred for reasons of availability.

When the "A" group is present, that is, when a is other than 0, each unit "A" includes a linear alkylene or substituted alkylene portion, i.e., $(CHR_4)_b$, $(CHR_5)_c$, or $(CHR_6)_d$, each containing between 1 and about 10 methylene or substituted methylene units. The alkylene portion of the first "A" group is attached to the amide nitrogen, and the heteroatom of the last "A" group is attached to the alkylene portion, the $(CH_2)_e$, of $R_3$. Examples of these alkylene portions include methylene, ethylene, n-propylene, n-butylene, n-octylene and n-decylene, each carbon of which may, optionally, carry a hydrocarbon substituent, $R_4$, $R_5$, and $R_6$. If $R_4$, $R_5$, and $R_6$ are not hydrogen, they are preferably lower alkyl groups, as described above.

Additionally, in each unit "A", the linear alkylene or substituted alkylene portion is bonded to an oxygen, sulfur, or nitrogen atom. Internally in the $(A)_a$ groups, the oxygen and sulfur atoms will be manifested in ether or thioether linkages. The internal nitrogen atoms will, in turn, appear as a secondary or tertiary amine linkage.

Pendant groups of the polymers of Formula 1, and in the corresponding formula in the claims, are terminated with a nitrogen-containing group that is capable of ionizing and ionically bonding with ionic groups of the bile acid molecules, as referred to above.

When the terminal group is an amino group, a relatively-high proportion of these amino groups (for example, 50 to 70% of the total number of amino groups) are protonated in the gut, which typically has a pH of about 7.2 to about 7.5. Such protonated amino groups are positively charged and capable of forming ionic bonds with negatively-charged groups on the molecules of bile acids.

When the terminal group is a quaternary ammonium group, these groups carry a permanent positive charge which is capable of forming ionic bonds with the aforementioned negatively-charged groups on the molecules of the bile acids.

Where $R_3$ is an amino group, it can be a primary ($-NH_2$), secondary

or tertiary

amine group. The substituent(s) of a secondary or tertiary group can be hydrocarbon groups or heteroatom-containing hydrocarbon groups as described above. For tertiary groups, the substituents can be the same or different.

Where $R_3$ is a quaternary ammonium group, that is,

the substituents can be hydrocarbon groups or heteroatom-containing hydrocarbon groups, as described above. These substituent groups may be the same or different. For example, these substituent groups may be oligomers of oxirane, 2-methyloxirane, aziridine, 2-methylaziridine, thiirane and 2-methylthiirane. Preferred hydrocarbon substituents are lower alkyl groups and oligomers of oxirane and aziridine, with the substituents being all the same or different.

The nitrogen atom of the terminal group $R_3$ of Formula 1, and of the corresponding formula in the claims, also has attached thereto a hydrocarbon linking group which links the nitrogen atom of the amino group or of the quaternary ammonium group to the heteroatom of the pendant group which is adjacent thereto, for example, to the oxygen, sulfur, or nitrogen atom where the "A" group is present, or with the nitrogen atom of the amide group if the "A" group is not present. The hydrocarbon linking group is an alkyl group consisting of one to 6 methylene groups, the number of the methylene groups being indicated in Formula 1 and in the corresponding formula in the claims by "e".

As mentioned above, polymers within the scope of the present invention include copolymers, which may be polymerized from mixtures of two or more monomers, and further including polymers in which fewer than all of the carbon atoms of the polymer's backbone have pendant groups, or polymers in which the pendant groups are not those described in Formula 1, that is, they are not the pendant

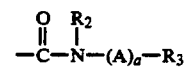

groups, or both. Such copolymers may be made, for instance, by copolymerizing monomers containing the structure of Formula 1 with one or more different monomers which either do not have pendant groups, or have pendant groups which are not the

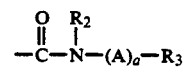

groups, or both. Preferably, the polymers of the present invention have the pendant

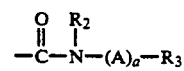

groups on about 30% or more of the carbon atoms the polymer backbone, and more preferably on about 50% or more of the carbon atoms of the polymer backbone. Examples of monomers which may be copolymerized with the monomers containing the structure of Formula 1 include hydroxymethylmethacrylamide, hydroxymethylacrylamide, methyl methacrylate and other lower alkyl methacrylates, lower alkyl acrylates, acrylamide, methacrylamide and olefins, for example, ethylene and isobutylene.

A preferred class of polymers of the present invention comprises those in which: "a" is 0 to about 5; when "a" is not 0, "A" is oxyalkyl and "b" is 1 to about 5 and $R_4$ is hydrogen, or "A" is aminoalkyl and "d" is 1 to about 5 and $R_6$ is hydrogen; and when "a" is zero or 1 to about 5, then $R_1$ is hydrogen or lower alkyl, $R_2$ is hydrogen or lower alkyl, and the nitrogen of $R_3$ is a tertiary amine substituted with lower alkyl groups or a quaternary ammonium group substituted with lower alkyl groups. The preferred polymers are water soluble or capable of forming colloidal dispersions, have a molecular weight mode of at least about 80,000 daltons, and have little or no crosslinking.

A particularly preferred class of compounds in accordance with the present invention comprises those in which: "a" is 0 or 1; when "a" is 1, "A" is aminoalkyl, with "d" being 1 to about 5 and $R_6$ being hydrogen; and when "a" is 0 or 1, then $R_1$ is hydrogen or methyl, $R_2$ is hydrogen or methyl, the linking group between the nitrogen atom of $R_3$ and the nitrogen atom of "A" or the nitrogen atom of the amide group is a straight chain alkylene group containing 3 to about 5 carbon atoms, with n-propylene and n-butylene being particularly preferred, and the nitrogen of $R_3$ is a tertiary amine substituted with two methyl groups. The particularly preferred class of compounds are water soluble, have a molecular weight mode of at least about 250,000, and have little or no crosslinking.

As used herein, the term, "little or no crosslinking" refers to levels of crosslinking, and correspondingly, the levels of crosslinking monomer polymerized into the polymer, from 0 to about 0.5% by weight of the total monomer. More preferred are polymers which have from 0 to about 0.05% crosslinking, and still more preferred are polymers which have no crosslinking. At levels of crosslinking above about 0.5%, the viscosity of the polymer is sufficiently high to make polymer preparation difficult by the procedures exemplified herein.

Among the particularly preferred members of Formula 1 are the homopolymers of dimethylaminopropylmethacrylamide (DMAPMA) and dimethylaminopropylacrylamide (DMAPA) which have the following structural formulas:

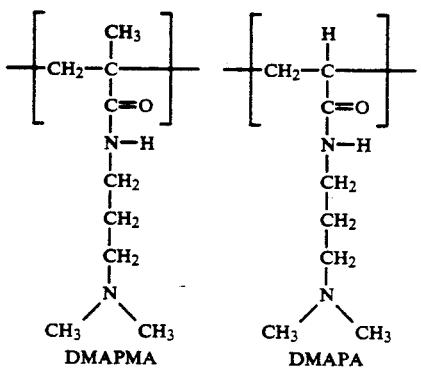

Examples of resins for use in the practice of the present invention are listed below:
poly(aminomethylacrylamide);
poly(aminomethylmethacrylamide);
poly(methylaminomethylacrylamide);
poly(methylaminomethylmethacrylamide);
poly(dimethylaminomethylacrylamide);
poly(dimethylaminomethylmethacrylamide);
poly(aminoethylacrylamide);
poly(aminoethylmethacrylamide);
poly(methylaminoethylacrylamide);
poly(methylaminoethylmethacrylamide);
poly(dimethylaminoethylacrylamide);
poly(dimethylaminoethylmethacrylamide);
poly(aminopropylacrylamide);
poly(aminopropylmethacrylamide);
poly(methylaminopropylacrylamide);
poly(methylaminopropylmethacrylamide);
poly(dimethylaminopropylacrylamide);
poly(dimethylaminopropylmethacrylamide);
poly(aminobutylacrylamide);
poly(methylaminobutylacrylamide);
poly(dimethylaminobutylacrylamide);
poly(aminobutylmethacrylamide);
poly(methylaminobutylmethacrylamide);
poly(dimethylaminobutylmethacrylamide);
poly(aminopentylacrylamide);
poly(methylaminopentylacrylamide);
poly(dimethylaminopentylacrylamide);
poly(aminopentylmethacrylamide);
poly(methylaminopentylmethacrylamide);
poly(dimethylaminopentylmethacrylamide);
poly((dimethylaminopropylmethacrylamide)-co-(acrylamide));
poly((dimethylaminopropylmethacrylamide)-co-(methacrylamide));
poly(1-amino-3,6-diazaheptylacrylamide); and
poly(1-amino-3, 6-diazaheptylmethacrylamide).

The polymeric amides of this invention can be prepared in several different ways. Syntheses which produce any significant amount of crosslinked polymer should be preferably avoided. Some basic methods of synthesis known heretofore can be applied to the preparation of the polymers of the present invention. Illustrative of known methods is the industrial preparation of poly(dimethylaminopropylmethacrylamide) disclosed in U.S. Pat. Nos. 4,359,540 and 4,382,853.

In preferred form, the synthesis should be capable of yielding high conversions of monomer to polymer and the polymer produced should have a molecular weight mode of at least about $2.5 \times 10^5$ daltons. (The term "molecular weight mode" means the statistically most probable molecular weight of a polymer chain among polymers having different molecular weights.) As there may be a tendency for relatively small size polymers to be adsorbed on the lining of the intestine where they can cause inflammational disorders, it is preferred that less than about 5 wt. % of the polymers have a size of about 50,000 daltons or less.

For therapeutic purposes, the polymer must be free of toxic materials, for example, monomeric and oligomeric components which would have a toxic effect on the body. High purity can be attained with high conversions in the polymer synthesis, but for satisfactory physiological use the polymer should be subjected to rigorous purification subsequent to polymerization. For the treatment of hypercholesterolemia in mammals, including humans, the polymeric amide preferably contains no more than about 1000 parts per million parts (ppm) by weight of the monomer from which the polymer is made, more preferably no greater than about 100 ppm, and still more preferably no greater than about 30 ppm by weight of the monomer.

One general technique by which the polymeric amides of the present invention can be made is by treating an appropriate acrylic polymer, such as poly(acrylamide) or poly(methacrylamide) with a desired oligomer "(A)" which has been separately synthesized. The oligomer "(A)" can be attached to the amide nitrogen via formaldehyde by methylolation of the amide nitrogen, followed by nucleophilic displacement by the terminal nucleophile from the oligomer on the methylol group of the amide. By this method, formaldehyde can be used to attach the desired tentacles to the polyamide backbones. Such chemistry for attaching tentacles to the linear polymeric backbones via the amide nitrogen falls within the scope of this invention.

Alternatively, appropriately reactive and structured amides can be polymerized as the last step of the process. In general, this technique is preferred, as higher conversions of purer product may be obtained when the polymerization is carried out as the last step. Thus, the synthesis of various polymeric amides within the scope of this invention may begin with the preparation of appropriate monomers.

Certain acrylamide monomers are particularly attractive for use in the practice of the present invention because they are commercially available and their polymerization leads to polymeric amides which have relatively good properties. For example, dimethylaminopropylacrylamide and dimethylaminopropylmethacrylamide can be obtained commercially and polymerized in the presence of a free radical initiator to give, respectively, poly(dimethylaminopropylacrylamide) and poly(dimethylaminopropylmethacrylamide) of high molecular weight and high conversions of monomer to polymer. These polymers, poly(DMAPA) and poly(DMAPMA) respectively, are presently particularly preferred polymeric amides within the scope of this invention.

Resins of this invention may be useful in the form of free bases or also in the form of acid salts, and preferably in the form of pharmaceutically acceptable salts, that is, salts whose anions are nontoxic to the involved organism in pharmaceutical doses of the salts, so that the beneficial pharmacological properties inherent in the free base are not vitiated by side effects ascribable to the anions. All such forms are within the scope of the invention. The resins, or salts or bases thereof, can be used to treat mammals, including humans, in neat form or as a constituent of a pharmaceutical composition which includes a pharmaceutically acceptable carrier.

Because the resins of the present invention, in their free base form, tend to remove chloride ion from the stomach, which can lead to electrolyte imbalance in the treated animal, partial conversion of the resins to the chloride salt is desired. As an example, the preferred form of poly(dimethylaminopropylmethacrylamide) is a salt in which 85% of the amine sites have been converted to the chloride by partial neutralization with hydrochloric acid, and 15% of the amine sites remain in the free base form. The pH of a 1-3% aqueous solution of this partially neutralized resin is between 6.5 and 7.5, compared with the free base resin itself, with a pH of 10.5. This formulation has shown essentially no effect on serum electrolyte levels even at high dosages of 600 mg/kg/day in three different animals: dogs, monkeys and rats.

Although pharmaceutically acceptable salts of the resin are preferred, all addition salts are useful as sources of the free base form even if the particular salt itself is desired only as an intermediate product, as for example, when the salt is formed only for purposes of purification and identification, or when it is used as an intermediate in preparing a pharmaceutically acceptable salt by ion exchange procedures.

Pharmaceutically acceptable salts of the compounds useful in the practice of this invention include, for example, those derived from the following acids: mineral acids such as hydrochloric acid, sulfuric acid, phosphoric acid and sulfamic acid; and organic acids such as acetic acid, citric acid, lactic acid, tartaric acid, malonic acid, benzenesulfonic acid, p-toluenesulfonic acid, cyclohexylsulfamic acid, quinic acid, and the like.

The acid addition salts of the resin of the present invention are prepared either by dissolving the free base in aqueous or aqueous-alcohol solution or other suitable solvents containing the appropriate acid and isolating the salt by evaporating the solution, or by allowing the free base to react with an acid in an organic solvent, in which case the salt separates directly or can be obtained by concentration of the solution.

The polymeric amides described above are especially attractive bile acid sequestrants. Preferred members of the series are 3-6 times more effective than the polymeric sequestrants, such as cholestyramine and cholestipol, described in the prior art, and the therapeutically effective dosages of these compounds can be lowered correspondingly. Furthermore, species of the polymeric amides are relatively water soluble. The latter feature makes members of the series much more convenient for the patient to ingest.

While the following explanation is not intended to be binding, the polymers of the present invention, including the polymeric amides described above, are believed to be more effective than the known resins because of the openness and flexibility of the tentacle-like linear chains attached to the backbone of the polymer, and the accessibility of bonding sites (including hydrogen bonding sites and ionic binding sites). The geometry of the polymers of this invention are also believed to readily admit and accommodate the bile acid anions with their surrounding hydration shells. Further, the accessibility to the bonding sites located on the flexible tentacles are believed to permit the bile acid anions to compete more effectively for those sites than the smaller $Cl-$, $HCO_3-$, $HSO_4-$, and $HPO_3-$ anions which are present in the intestine.

The dosage of the polymers of the present invention that will be most suitable for treatment will vary with the form of administration, the particular polymer chosen, and the physiological characteristics of the particular host under treatment. The therapeutic human dosage, based on physiological studies using dogs, will generally be from about 2 to about 125 mg/kg of body weight per day or about 0.2 to about 10 g/day. It is expected that more widely used dosages will be about 35 to about 50 mg/kg of body weight per day or about 3 to about 4 g/day. The polymers of this invention are not absorbed from the digestive tract into the blood or lymph plasma and therefore, have very low or no toxicity toward mammals.

The polymers of this invention can be administered in any suitable way. Since they function in the digestive tract, oral administration is recommended. The polymers may be ingested in various forms, including in neat form or as a therapeutic preparation in which it is combined with a pharmaceutically acceptable carrier. The therapeutically effective amount of polymer will vary, depending upon the type of preparation but will generally lie in the range of about 100 mg to about 10 gm per dosage unit.

To the extent polymers of this invention are water-soluble, pharmaceutically acceptable diluents, carriers, or excipients with which the polymer can be mixed to produce a therapeutic preparation include a number of different types of food, such as vegetable products, for example, vegetable juices and stewed vegetables, and fruits, for example, fruit juices, apple sauce and stewed fruits, and cereals, etc. The polymers are essentially tasteless, and such foods are the preferred pharmaceutically acceptable carriers.

However, a number of conventional pharmaceutical formulations can also be employed. Therapeutic preparations in the form of tablets, capsules, syrups, elixirs, and suspensions can be used effectively. Unit dosages of up to about 1 gram can be accommodated in tablets.

The polymers of the present invention can be used in combination with other treatments which are designed to lower the level of cholesterol in the blood. In preferred form, a polymer of the present invention is used in combination with a material which is effective in inhibiting the synthesis of cholesterol in the liver of a host. While any available material having such characteristics can be used, the material is preferably one which is effective in inhibiting the formation of cholesterol in the liver by inhibiting HMG coenzyme A reductase. A particularly preferred material for this purpose is lovastatin (for example, see U.S. Pat. No. 4,231,938). Examples of other types of material which can be used are simvastatin and pravastatin (for example, see respectively U.S. Pat. Nos. 4,444,784 and 4,346,227). Other types of inhibitors of the biosynthesis of cholesterol in the liver can be used in combination with the polymers of the present invention.

The polymer of the present invention can be used with the aforementioned type cholesterol-inhibiting material in separate treating steps or in the form of a composition comprising an admixture of the aforementioned. Although the amounts of the constituents comprising the composition can vary over a wide range, a composition comprising about 95 to about 99.5 wt. % of the polymer of the present invention and about 0.5 to about 5 wt. % of the cholesterol-inhibiting material is believed to have relatively wide applicability for treating hypercholesterolemia. A preferred form of the composition comprises about 97 to about 98.5 wt. % of the polymer of the present invention and about 1.5 to about 3 wt. % of the cholesterol-inhibiting material. The dosage of such compositions can be about 0.5 to about 4.5 g/day, preferably about 1 to about 2 g/day.

Examples which follow are illustrative of the practice of the present invention. All percentages and ratios are by weight unless otherwise specified, and all reagents used are of good commercial quality unless otherwise specified.

EXAMPLES 1 to 22

These examples illustrate preparation, under different conditions, of poly(dimethylaminopropylmethacrylamide) polymers of the present invention.

A mixture of 1.2254 g ($4.9337 \times 10^{-3}$ mole) of Vazo 52 initiator (2,2'-Azobis(2,4-dimethylvaleronitrile)) dissolved in 700.0 g (4.111 moles) of dimethylaminopropylmethacrylamide (DMAPMA) monomer was poured into a five liter, four-necked round-bottomed glass flask. The molar ratio of Vazo 52 initiator to monomer was $1.2 \times 10^{-3}$ to 1. To the flask was added 2800 g (155.4 moles) of deionized water. The flask was fitted with a heating mantle which was connected to a microprocessor for control of the-time-temperature profile, a stirrer, a thermistor for temperature sensing, a condenser cooled by chilled (2° C.) water, a nitrogen inlet for sparging the system free of oxygen, and a sampling port capped with a rubber dam through which samples may be thieved via a large bore stainless steel syringe. The thermistor was wired to the microprocessor to provide the temperature input to the microprocessor. The stirring rate was set at 65 to 100 rpm, and the stirring was started. Nitrogen was passed through the liquid via a sintered glass sparging tube at a flow rate of 1.10 liters per minute for two hours in order to de-oxygenate the liquid and the gas environment completely. The nitrogen flow rate was reduced to 0.20 liter per minute during the polymerization step, so that the reactor volume turnover during the de-oxygenation step was 0.220 per minute and during the polymerization step is 0.040 per minute.

With the above procedure, 22 different resins were made by conducting 22 polymerizations of DMAPMA and by varying certain of the parameters of the reaction as described hereafter. The microprocessor was programmed to heat the reaction mixture from ambient temperature to the temperature at which the reaction mixture was held, as indicated in Table 1 below, at a particular rate, that is, at a predetermined number of Celsius degrees per minute. Such a rate is called a "ramping rate". Table 1 below identifies, for each of the polymerizations, the ramping rate, the temperature at which the mixture was held for polymerization, and the time of heating the reaction mixture, measured from the time the mixture first reached the temperature of polymerization to the time when cooling of the mixture to ambient temperature was begun.

The viscosity of a 20% polymer solution in water varies between about 6000 and 12,000 centipoises at 25° C. The properties of the final products prepared via this procedure are tabulated in Table 1. The column headed "% CONVER" indicates the percent conversion of the monomer to polymer.

TABLE 1

| DMAPMA POLYMERS AND PROPERTIES | | | | | | |
|---|---|---|---|---|---|---|
| Ex | Ramping Rate C.°/Min | Temp °C. | Time, Hrs | M/W MODE, Daltons | Mw/Mn | % CONVER | % MW < than 50,000 Daltons |
| 1 | 2 | 52 | 20 | 406100 | 3.34 | 88.00 | 3.32 |
| 2 | 2 | 52 | 20 | 406100 | 3.46 | 91.50 | 3.47 |
| 3 | 2 | 52 | 20 | 208400 | 3.28 | 92.30 | 4.45 |
| 4 | 2 | 52 | 20 | 337500 | 3.38 | 91.60 | 4.23 |
| 5 | 0.17 | 50.5 | 138 | 402639 | 3.73 | 97.54 | 5.35 |
| 6 | 0.17 | 51.5 | 138 | 335323 | 3.54 | 97.59 | 5.60 |
| 7 | 0.25 | 49.2 | 113 | 415840 | 3.65 | 98.19 | 4.40 |
| 8 | 0.25 | 55 | 113 | 275641 | 2.92 | 98.59 | 4.91 |
| 9 | 0.5 | 52 | 111 | 325383 | 3.07 | 98.09 | 4.43 |
| 10 | 0.1 | 45 | 100 | 414384 | 3.65 | 98.54 | 4.11 |
| 11 | 0.1 | 45 | 100 | 414384 | 3.36 | 98.04 | 3.32 |
| 12 | 1.0 | 45 | 100 | 414384 | 3.61 | 98.53 | 4.07 |
| 13 | 1.0 | 52 | 96 | 365215 | 3.18 | 98.75 | 4.30 |
| 14 | 1.0 | 52 | 96 | 306503 | 2.91 | 98.42 | 4.85 |
| 15 | 1.0 | 52 | 96 | 411894 | 3.09 | 98.64 | 3.57 |
| 16 | 1.0 | 52 | 96 | 435879 | 3.5 | 98.58 | 5.01 |
| 17 | 1.0 | 52 | 96 | 364769 | 3.44 | 98.26 | 5.72 |
| 18 | 1.0 | 52 | 96 | 364769 | 3.68 | 98.23 | 6.26 |
| 19 | 1.0 | 51 | 96 | 324300 | 3.29 | 98.69 | 4.87 |
| 20 | 0.5 | 52 | 100 | 291850 | 3.11 | 97.37 | 4.04 |
| 21 | 0.5 | 51.5 | 98.45 | 402639 | 3.95 | 98.10 | 5.04 |
| 22 | 0.5 | 52 | 115.25 | 233510 | 3.29 | 98.89 | 6.36 |

As may be seen from Table 1 above, the molecular weight mode of the poly(DMAPMA) resins ranges between about $2.3 \times 10^5$ and $4.4 \times 10^5$ daltons. The molecular size distribution is broad, and the polydispersity ($M_w/M_n$) varies between about 2.9 and 4.0. The conversion of monomer to polymer reaches 97 to 98% of theory after about 100 hours at 52° C., as assessed by capillary-GLC measurements.

To reduce the quantity of unreacted monomer remaining with the polymer, the aqueous solution of polymer was diluted from a concentration of about 20% polymer to about 5% polymer by adding deionized water. The dilute solution was then passed through an ultrafiltration unit. Ultrafiltration reduced the monomer content from between about 25,000 and 30,000 ppm to below about 1,000 ppm. The step of ultrafiltration can also be used to provide a polymeric composition that contains less than about 5 wt. % of polymers which have a size of 50,000 daltons or smaller.

The polymers may be de-watered effectively by any of the following methods to give a white powder: drum drying, spray drying, lyophilizing or freeze-drying. Most of the materials used in the animal feeding studies described below were de-watered on the drum drier, but the lyophilized materials have the most desirable texture, and lyophilizing is the preferred method. The de-watered polymeric powder has a moisture content ranging between about 0 and 6 wt. %.

EXAMPLES 23 AND 24

These examples illustrate preparation of additional samples of poly(dimethylaminopropylmethacrylamide).

As described in Example 1, six 5-liter polymerizations of DMAPMA were carried out in a similar fashion except for the initiator, the polymerization-temperature profile, and the aqueous phase. Vazo 67 initiator, 2,2'-azobis(2-methylbutyronitrile), was substituted for Vazo 52 at the same molar ratio of $1.2 \times 10^{-3}$ mole initiator to mole of monomer. The reaction temperature profile was 1.0° C. per minute from 25° to 70° C., a plateau at 70° C. for four hours, a ramp to 95° C. at 1.0° C. per minute, and a plateau at 95° C. for four hours. The aqueous phase, instead of being only deionized water, was a solution of 4.0 wt. % sodium chloride and 1.33 wt. % Triton X-405 surfactant dissolved in deionized water. With the time-temperature profile described, the total reaction time was 9.17 hours, at which point the conversion of monomer to polymer was approximately 90% of theory. The measured conversion and the molecular size characteristics are given in Table 2 where the 6 batches of resin are identified as Ex. 23-A, -B, -C and Ex. 24-A, -B, -C. The three 5-liter "23" batches were combined to give a lot of product referred to herein as "Ex. 23" and the three 5-liter "24" batches were combined to give a lot of product referred to herein as "Ex. 24". The combined batches were freed of monomer and low molecular weight oligomers by ultrafiltration, followed by concentration and dewatering on a drum drier to provide a light tan powder for the assessment of efficacy.

TABLE 2

POLY(DMAPMA)

| Ex. | MW Range | % MW < 50K | MW Mode | $M_n$ | $M_w$ | $M_w/M_n$ | Conv. |
|---|---|---|---|---|---|---|---|
| 23-A | 3,998 to 6,258,133 | 12.53 | 321,383 | 90,500 | 465,000 | 5.1 | 86.3 |
| -B | 8,193 to 5,720,841 | 9.69 | 478,170 | 121,000 | 655,000 | 5.4 | 91.6 |
| -C | 7,117 to 7,313,689 | 10.56 | 386,732 | 110,200 | 632,400 | 5.7 | 92.8 |
| 24-A | 5,870 to 8,400,000 | 8.45 | 317,000 | 122,200 | 658,400 | 5.4 | nr* |
| -B | 5,314 to 10,400,000 | 8.19 | 373,500 | 125,400 | 698,500 | 5.6 | nr* |
| -C | 5,706 to 10,400,000 | 8.49 | 317,000 | 123,500 | 688,700 | 5.6 | nr* | nr* — not recorded

The polymeric compositions of each of the examples of Table 2 can be additionally treated by ultrafiltration to reduce further the content of low molecular weight polymers, that is, so that less than about 5 wt. % of the polymers have a size of 50,000 daltons or less.

EXAMPLE 25

This example illustrates another preparation of poly(-dimethylaminopropylmethacrylamide) polymers of the present invention.

By a method similar to that described in Example 1, dimethylaminopropylacrylamide (DMAPA) monomer was transformed into its polymer by treating 330.0 g (2.112 moles) DMAPA with 0.396 g ($2.5347 \times 10^{-3}$ mole) of 2,2'-azobis(2,4-dimethylvaleronitrile) initiator at 52° C. for 101 hours. The polymerization was conducted in a two-liter, four-necked, round-bottomed glass flask with a 20% (weight) aqueous solution of the monomer in 1320.0 g (73.271 moles) deionized water. As in Example 1, oxygen was removed from the liquid with nitrogen for two hours at ambient temperature, a nitrogen flow rate of 0.44 liter per minute and a slow agitation rate, about 60 rpm. The nitrogen flow rate was reduced to 0.08 liter per minute during the polymerization step, so that the reactor volume turn over during the de-oxygenation step was 0.220 per minute and during the polymerization step was 0.040 per minute. The time-temperature profile was controlled by a microprocessor, as described in Example 1, to the following: a heat-up rate of 0.1 C° per minute from 25° to 52° C. for an elapsed time of 4.5 hours and a holding temperature at 52°±1° C. for 101 hours. The aqueous solution of the polymeric composition was cooled to ambient temperature and assessed for molecular weight and percent conversion of monomer to polymer. The percent conversion was 94.6, and the molecular size distribution was found to be the following.

| Molecular Size | |
|---|---|
| Range | 3,500 to 2,409,000 |
| $M_w$ Mode | 127,876 |
| $M_n$ | 56,900 |
| $M_w$ | 162,500 |
| $M_w/M_n$ | 2.86 |
| MW < 50k | 20.5 wt. % |

The polymeric composition of Example 25 can be additionally treated by ultrafiltration to reduce further the content of low molecular weight polymers, that is, so that less than about 5 wt. % of the polymers have a size of 50,000 daltons or smaller.

EXAMPLE 26

This example illustrates the efficacy of the polymers of the present invention for lowering plasma levels of cholesterol in a host.

To assess the effectiveness of resins of the present invention in lowering blood plasma cholesterol levels, samples of the resins were evaluated in in vivo tests in beagle dogs. Beagle dogs weighing 10 to 13 kg each are fed the resins admixed with a semi-synthetic, low cholesterol diet (described below). The animals were fed once a day. Normal plasma cholesterol levels were assessed for each dog by feeding the semi-synthetic diet without a bile-acid sequestrant for six months while measuring plasma cholesterol levels on blood samples taken twice a week. Blood samples were taken on Tuesdays and on Thursdays. After each dog was tracked for six months, cholestyramine (for comparative purposes) was mixed with the daily portion of diet at 3, 6, and 12 grams for four consecutive weeks at each dosage in order to titrate the response as a function of dosage. After the dog had been tracked and characterized for its response to cholestyramine, the dog was kept on a regimen of 12 grams cholestyramine per day until the resin sample of the present invention was substituted for the cholestyramine. Dosages of the resin samples were begun at either 3 or 6 grams per day, and the plasma level of cholesterol was monitored for 21 days.

For more efficacious materials, the plasma cholesterol level decreases and plateaus at some lower level. For less efficacious materials, the plasma level of cholesterol increases and levels off at some higher plasma concentration. The concentration plateau that is reached is related to that of feeding 12 grams of cholestyramine per day, and the efficacy factor is computed via the following equation:

$$\text{Efficacy Factor} = \left(\frac{N - B}{N - A}\right)\left(\frac{12}{X}\right)$$

where

N = plasma cholesterol level in mg/dl of blood on semi-synthetic diet without a bile-acid sequestrant A = plasma cholesterol level in mg/dl of blood on semi-synthetic diet mixed with 12 grams cholestyramine per day B = plasma cholesterol level in mg/dl of blood on semi-synthetic diet mixed with x grams per day of resin sample of the invention X = grams of experimental material admixed with food per day.

Table 3, below, includes the measured values from the feeding studies along with the calculated efficacy factors. The higher the efficacy factor, the more potent the resin sample is than cholestyramine administered at a regimen of 12 grams per day. An efficacy factor of one would indicate that the comparative sample is equivalent to cholestyramine. An efficacy factor of five would reveal that, at one-fifth the dosage, the comparative sample is effective in reducing the blood plasma level of cholesterol equivalent to that of a 12-gram daily regimen of cholestyramine.

The composition of the semi-synthetic diet is given below and is fed to the dogs in a quantity (200 to 300 grams per dog per day) that stabilizes the dog's body weight.

| Composition of Semi-synthetic Diet | |
| --- | --- |
| 1. Vitamin free casein | 32.01% |
| 2. Dextrose | 43.14% |
| 3. Lard | 12.42% |
| 4. Cod liver oil | 2.39% |
| 5. Calcium phosphate | 2.72% |
| 6. Celluflour | 4.92% |
| 7. Hegsted salt and vitamin mix no. 14 | 2.39 |

The measured results from the dog feeding studies are tabulated in Table 3.

TABLE 3

| Dog | Treatment | Level of Cholesterol in Blood Plasma mg/dl | % Decrease | Efficacy Factor over cholestyramine at 12 g/day Feeding |
| --- | --- | --- | --- | --- |
| A | control | 140 | | |
| | cholestyramine, 3 g/day | 124 | 11.4 | |
| | cholestyramine, 6 g/day | 107 | 23.6 | |
| | cholestyramine, 12 g/day | 97 | 30.7 | |
| | polymer, Ex. 24, 6 g/day | 75 | 46.4 | 3.02 |
| B | control | 165 | | |
| | cholestyramine, 3 g/day | 137 | 17.0 | |
| | cholestyramine, 6 g/day | 124 | 24.8 | |
| | cholestyramine, 12 g/day | 116 | 29.7 | |
| | polymer, Ex. 24, 3 g/day | 124 | 24.8 | 3.35 |
| C | control | 144 | | |
| | cholestyramine, 3 g/day | 111 | 22.9 | |
| | cholestyramine, 6 g/day | 112 | 22.2 | |
| | cholestyramine, 12 g/day | 96 | 33.3 | |
| | polymer, Ex. 24, 3 g/day | 103 | 28.5 | 3.42 |
| | polymer, Ex. 23, 6 g/day | 78 | 45.8 | 2.75 |
| D | control | 96 | | |
| | cholestyramine, 3 g/day | 89 | 7.3 | |
| | cholestyramine, 6 g/day | 76 | 20.8 | |
| | cholestyramine, 12 g/day | 73 | 23.9 | |
| | polymer, Ex. 24, 3 g/day | 75 | 21.9 | 3.65 |
| E | control | 134 | | |
| | cholestyramine, 3 g/day | 127 | 5.2 | |
| | cholestyramine, 6 g/day | 112 | 16.4 | |
| | cholestyramine, 12 g/day | 95 | 29.1 | |
| | polymer, Ex. 23, 1 g/day | 126 | 6.0 | 3.43 (3 g) 2.46 |
| | polymer, Ex. 23, 2 g/day | 117 | 12.7 | 2.32 (6 g) 2.62 |
| | polymer, Ex. 23, 3 g/day | 81 | 39.6 | 5.44 |
| | polymer, Ex. 24, 3 g/day | 100 | 25.4 | 3.49 |
| | polymer, Ex. 24, 6 g/day | 71 | 47.0 | 3.23 |
| F | control | 129 | | |
| | cholestyramine, 3 g/day | 111 | 13.9 | |
| | cholestyramine, 6 g/day | 104 | 19.4 | |
| | cholestyramine, 12 g/day | 90 | 30.2 | |
| | polymer, Ex. 22, 6 g/day | 56 | 56.6 | 3.74 |
| G | control | 117 | | |
| | cholestyramine, 3 g/day | 107 | 8.5 | |
| | cholestyramine, 6 g/day | 99 | 15.4 | |
| | cholestyramine, 12 g/day | 85 | 27.3 | |
| | polymer, Ex. 23, 3 g/day | 90 | 23.1 | 3.38 |
| | polymer, Ex. 24, 3 g/day | 88 | 24.8 | 3.62 |
| | polymer, Ex. 24, 6 g/day | 52 | 55.6 | 4.06 |
| H | control | 140 | | |
| | cholestyramine, 3 g/day | 132 | 5.7 | |
| | cholestyramine, 6 g/day | 121 | 13.6 | |
| | cholestyramine, 12 g/day | 99 | 29.3 | |
| | polymer, Ex. 23, 1 g/day | 119 | 15.0 | 6.63 (6 g) 6.15 |
| | polymer, Ex. 24, 3 g/day | 101 | 27.8 | 3.80 |
| | polymer, Ex. 24, 6 g/day | 85 | 39.3 | 2.68 |

From the above examples, the polymeric materials of this invention are readily recognized as effective therapeutic agents for the control of the blood cholesterol level in mammals.

EXAMPLE 27

This example illustrates preparation of a polymer of the present invention which terminates in a quaternary amine group.

Poly(DMAPMA) was prepared in a 400-liter reactor using scaledup reactant ratios of Example 1. The reaction mixture was heated at approximately 0.5° C./minute to 52° C. and held at that temperature for 90 hours, after which the mixture was allowed to cool. The molecular-weight mode of the resulting polymer was 327,000 daltons, the $M_w/M_n$ ratio was 3.70, the conversion of monomer to polymer was 96.01%, and the percentage of material with a molecular weight less than 50,000 was 5.29. The poly(DMAPMA) was purified by passing it through an ultrafiltration apparatus for 10 volume replacements, and was diluted to an aqueous solution containing 4.75% poly(DMAPMA) for preparation of the polymer of this example. The poly(DMAPMA) contained less than 50 ppm residual monomer.

A sample of 1831.1 grams of the aqueous poly(DMAPMA) solution was charged to a 2-liter, stainless-steel Parr autoclave equipped with a temperature sensor and two ports fitted with needle valves. The autoclave was sealed and the solution was stirred at 100 rpm while heating it to 60° C. at 0.75° C./minute. After the autoclave contents had equilibrated at 60° C., pressurized chloromethane gas was introduced into the autoclave through a needle valve until the pressure in the autoclave had risen to 380 kiloPascals (kPa). The solution was allowed to react with the chloromethane at a pressure between 380 and 210 kPa, with additional chloromethane being added as the pressure fell, until a weight of chloromethane had been added that was equal to the theoretical amount of chloromethane that would react with the poly(DMAPMA) present. After this amount of chloromethane had been added, the autoclave contents were allowed to react until the pressure fell to zero, a total time of approximately 40 hours. The total amount of chloromethane added was 26.0 grams, or 0.515 moles. Chlorine analysis on the autoclave contents subsequent to reaction indicated that 82.41% of the original poly(DMAPMA) had been converted to the quaternary ammonium form. The properties of the product polymer are shown in Table 4, below:

TABLE 4a

| Percent Polymer with Molecular Weight Less than 50,000: | 1.71 ± .03 |
| --- | --- |
| Molecular Weight Mode: | 553000 ± 1000 |
| Number-Average Molecular Weight ($M_n$): | 280233 ± 4143 |
| Weight-Average Molecular Weight ($M_w$): | 731867 ± 7257 |
| Z-Average Molecular Weight ($M_z$): | 1432667 ± 32331 |
| $M_w/M_n$: | 2.61 ± 0.03 |

TABLE 4b

| | Elemental Analysis | |
| --- | --- | --- |
| Element | Measured | Theoretical |
| % C | 53.30 | 54.41 |
| % H | 9.56 | 9.588 |
| % N | 12.03 | 12.691 |
| % O | 10.91 | 7.248 |
| % Cl | 13.79 | 16.06 |

EXAMPLE 28

This example illustrates preparation of the amine oxide derivative of poly(DMAPMA), another polymer of the present invention. This derivative has the following terminal nitrogen-containing group:

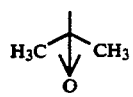

A 3000.7-gram charge (0.8370 equivalents of amino groups) of the aqueous poly(DMAPMA) solution of Example 27 was added to a 5-liter, 4-neck, round-bottom flask equipped with a stirrer, condenser, temperature sensor and liquid inlet port. The solution was stirred at 155 rpm while adding, dropwise over 90 minutes at ambient temperature, 95.05 grams of 30% aqueous hydrogen peroxide solution (0.8383 moles). The mixture was stirred for two hours at ambient temperature, then heated to 40° C. over a 2-hour period and held at 40° C. for another two hours. The infra-red spectrum of the resulting polymeric product indicated essentially complete conversion to the amine oxide. The properties of the product polymer were determined and are shown in Table 5, below:

TABLE 5a

| Percent Polymer with Molecular Weight Less than 50,000: | 3.52 |
| --- | --- |
| Molecular Weight Mode: | 373000 |
| Number-Average Molecular Weight ($M_n$): | 187100 |
| Weight-Average Molecular Weight ($M_w$): | 487900 |
| Z-Average Molecular Weight ($M_z$): | 926700 |
| $M_w/M_n$: | 2.61 |

TABLE 5b

| | Elemental Analysis | |
| --- | --- | --- |
| Element | Measured | Theoretical |
| % C | 55.21 | 58.04 |
| % H | 9.66 | 9.74 |
| % N | 13.97 | 15.04 |
| % O | 19.59 | 17.18 |

EXAMPLE 29

This example illustrates preparation of a low-molecular-weight poly(DMAPMA) polymer of the present invention. The molecular-weight mode of this polymer is approximately 80,000 daltons.

A monomer solution was prepared in a 500-ml flask by charging 100.69 g DMAPMA monomer to the flask and adding, with stirring, 1.8389 g ($7.4 \times 10^{-3}$ moles) of 2,2-azobis(2,4-dimethylvaleronitrile) initiator. A 2-liter, 4-neck, round-bottom reaction flask equipped with a stirrer, condenser, temperature sensor and ports for a nitrogen sparge and liquid addition was separately charged with 450.10 g DMAPMA monomer, to which 975.6 g deionized water was added with stirring. The 500-ml flask and the reaction flask were sparged with nitrogen for at least 10 flask volumes, and the contents of both flasks were maintained under a positive nitrogen pressure. The contents of the reaction flask were heated at 1° C./minute to 88° C. and held at that temperature while the initiator solution was transferred all at once from the 500-ml flask to the reaction flask. The contents of the reaction flask were maintained at 88° C. for 15 minutes after the initiator addition, then cooled in an ice bath to 52° C. and held at that temperature for 20 hours before being allowed to cool. The properties of the poly(DMAPMA) were measured and are shown below in Table 6.

TABLE 6

| Percent Polymer with Molecular Weight Less than 50,000: | 33.28 ± 0.83 |
| --- | --- |
| Molecular Weight Mode: | 76000 |
| Number-Average Molecular Weight ($M_n$): | 42000 |
| Weight-Average Molecular Weight ($M_w$): | 141000 |
| Z-Average Molecular Weight ($M_z$): | 485000 |
| $M_w/M_n$: | 3.40 |
| Conversion of Monomer to Polymer: | 73.56% |

EXAMPLE 30

This example illustrates preparation of a polymer according to the present invention from dimethylaminohexylmethacrylamide (DMAHMA). This required a two-part reaction, first to prepare DMAHMA from dimethylaminohexylamine, and then to polymerize the DMAHMA.

A 100-ml, round-bottom flask was equipped with a condenser and a port for adding liquid. To this flask 14.53 g methacryloyl chloride (90% purity, 0.1251 moles methacryloyl chloride) were charged. The flask was sparged with nitrogen for ten flask volumes, then 16.40 g dimethylaminohexylamine (DMAHA; 95% purity, 0.1080 moles DMAHA) were added dropwise, with stirring, to the flask contents. During the addition the temperature was maintained at 20° to 25° C. by cooling in an ice bath and by modulating the rate of DMAHA addition. The reaction was considered complete when the exotherm ceased. The flask was then opened, the contents were mixed with 30.8 g deionized water; the resulting monomer mixture contained 43.53% DMAHMA hydrochloride.

The reaction vessel for polymerization was a 250-ml, 3-neck, round-bottom flask equipped with a stirrer, temperature sensor, condenser and port for gas sparging. To this was charged 20.83 g of the DMAHMA hydrochloride mixture prepared above (0.08373 moles DMAHMA monomer) and 0.1003 g 2,2-azobis(2,4-dimethylvaleronitrile) initiator. Deionized water was added to dilute the mixture to 20% solids, and the pH of the mixture was adjusted to 8.5 with 50% aqueous sodium hydroxide solution. The flask was sparged with nitrogen for 10 flask volumes, and then maintained under positive nitrogen pressure throughout the reaction. The flask contents were heated at 1° C./minute to 60° C. and held at that temperature for 20 hours. The resulting polymer solution was ultrafiltered, and the molecular size parameters are shown in Tables 7 and 8 for both the untreated polymer and the ultrafiltered polymer.

TABLE 7

| Poly(DMAHMA) As Made | |
| --- | --- |
| Percent Polymer with Molecular Weight Less than 50,000: | 16.22 ± 0.46 |
| Molecular Weight Mode: | 191000 ± 3606 |
| Number-Average Molecular Weight ($M_n$): | 80953 ± 1652 |
| Weight-Average Molecular Weight ($M_w$): | 308867 ± 49533 |
| Z-Average Molecular Weight ($M_z$): | 755100 ± 153725 |
| $M_w/M_n$: | 3.81 ± 0.57 |

TABLE 8

| Poly(DMAHMA) After Ultrafiltration | |
| --- | --- |
| Percent Polymer with Molecular Weight Less than 50,000: | 17.23 ± 0.69 |
| Molecular Weight Mode: | 189667 ± 577 |
| Number-Average Molecular Weight ($M_n$): | 75107 ± 5299 |
| Weight-Average Molecular Weight ($M_w$): | 273367 ± 3177 |
| Z-Average Molecular Weight ($M_z$): | 681167 ± 4631 |
| $M_w/M_n$: | 3.65 ± 0.22 |

EXAMPLE 31

This example illustrates preparation of a lightly cross-linked polymer of the present invention from DMAPMA monomer crosslinked with 0.05 mole % ethylenebis(acrylamide).

A 0.2224 g charge ($1.32 \times 10^{-3}$ mole) of ethylenebis(acrylamide) crosslinker was introduced to a 250-ml, 4-neck, round-bottom flask equipped with a stirrer, condenser, temperature sensor and inlet ports for gas and liquid. The crosslinker was dissolved in 51.83 g DMAPMA monomer with stirring.

A 3.1436 g charge ($1.27 \times 10^{-2}$ mole) of 2,2-azobis(2,4-dimethylvaleronitrile) initiator was introduced to a 2-liter, 4-neck, round-bottom flask equipped with a stirrer, condenser, temperature sensor and inlet ports for gas and liquid. To this was added 423.1 g DMAPMA monomer; the mixture was stirred for 45 minutes to dissolve the initiator. 1029.0 Grams deionized water were then added to the flask.

Both flasks were sparged with nitrogen for at least 10 flask volumes, and the reaction flask was kept under a slight positive nitrogen pressure throughout the reaction. The contents of the 2-liter flask were heated at 1° C./minute from 25° C. to 60° C. and held at that temperature, and addition of the crosslinker solution from the 250-ml flask was immediately begin at approximately 0.13 ml/minute and continued over a period of 6.7 hours. The reaction was allowed to continue at 60° C. for a total of 20 hours from the start of the crosslinker addition. The total DMAPMA charge represented 2.657 moles of pure DMAPMA, and the ethylenebis(acrylamide) was $1.32 \times 10^{-3}$ moles. The properties of the resulting, crosslinked poly(DMAPMA) were determined, and are shown in Table 9, below.

TABLE 9

| | |
| --- | --- |
| Actual Crosslinker Percentage | 0.0497 |
| Percent Polymer with Molecular Weight Less than 50,000: | 9.81 ± 0.19 |
| Molecular Weight Mode: | 255667 ± 577 |
| Number-Average Molecular Weight ($M_n$): | 110300 ± 2646 |
| Weight-Average Molecular Weight ($M_w$): | 340267 ± 5345 |
| Z-Average Molecular Weight ($M_z$): | 713967 ± 30974 |
| $M_w/M_n$: | 3.09 ± 0.03 |

EXAMPLE 32

This example illustrates preparation of a lightly crosslinked polymer of the present invention from DMAPMA monomer crosslinked with 0.5 mole % ethylenebis(acrylamide).

The equipment and procedure of Example 31 were used, with the following exceptions. The initiator solution was prepared with 2.2214 g ($1.32 \times 10^{-2}$ moles) of ethylenebis(acrylamide) and 101.79 g DMAPMA monomer, and the DMAPMA monomer charge to the 2-liter reaction flask was 423.5 g; the total DMAPMA charge was 2.939 moles pure DMAPMA monomer. The contents of the reaction flask were observed to gel by the end of the 20-hour reaction period, so they were diluted with 450 g deionized water and re-heated to 60° C. to facilitate removal from the flask. The reacted mixture was finally diluted with deionized water to 15.67% solids. The properties of the polymer were determined and are shown below in Table 10.

TABLE 10

| | |
| --- | --- |
| Actual Crosslinker Percentage: | 0.449 |
| Percent Polymer with Molecular Weight Greater than 50,000: | 8.79 ± 0.06 |
| Molecular Weight Mode: | 304000 |
| Number-Average Molecular Weight ($M_n$): | 131700 ± 2650 |
| Weight-Average Molecular Weight ($M_w$): | 778366 ± 1069 |
| Z-Average Molecular Weight ($M_z$): | 2624333 ± 29501 |

TABLE 10-continued $M_w/M_n$: 5.91 ± 0.14

What is claimed is:

1. A polymeric composition comprising polymers having units of the structure

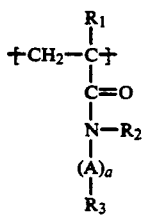

wherein

A is an aminoalkyl group $-(CHR_6)_d-NR_7-$, the alkyl being attached to the amide nitrogen;

a is an integer between 0 and about 10;

d is independently integers between 1 and about 10;

$R_1$ is hydrogen or a $C_1-C_8$ hydrocarbon group, $R_2$, $R_6$ and $R_7$ are independently hydrogen, hydrocarbon groups or heteroatom-containing hydrocarbon groups; and

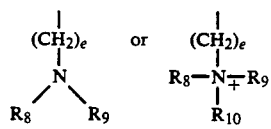

$R_3$ is e is an integer from 1 to 6, and $R_8$, $R_9$ and $R_{10}$ are independently hydrogen, hydrocarbon groups or heteroatom-containing hydrocarbon groups, the composition being nontoxic and the polymers having a molecular size distribution with a mode of about 80,000 daltons or greater and from 0 to about 0.5 percent crosslinking.

2. The composition of claim 1 containing less than about 5 weight percent polymers with a size of about 50,000 daltons or less.

3. The polymeric composition of claim 1 containing about 1000 or fewer parts, by weight, of monomer from which the polymers were made per million weight parts of the polymers.

4. The polymeric composition of claim 2 containing about 1000 or fewer parts, by weight, of monomers from which the polymers were made per million weight parts of the polymers.

5. The composition of claim 1 wherein the mode is at least about 250,000 daltons and wherein the composition contains no more than about 100 parts, by weight, of monomers from which the polymers are made per million weight parts of the polymers.

6. The composition of claim 1 which is water-soluble.

7. The composition of claim 1 which is a colloidal dispersion.

8. The composition of claim 1 wherein the pendant

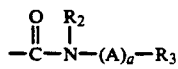

groups have sites capable of forming ionic bonds with bile acid anions and sites capable of forming hydrogen bonds with hydroxyl groups of bile acids, and wherein the bile acid anions are the anions of conjugate acids formed by the reaction of bile acids with glycine and with taurine.

9. The composition of claim 1 wherein the polymers are copolymers and wherein at least 30 percent of the repeating units of the backbone of the polymers have the pendant

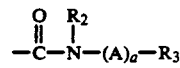

groups.

10. The composition of claim 1 wherein the polymers are copolymers and wherein at least 50 percent of the repeating units of the backbone of the polymers have the pendant

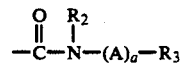

groups.

11. The composition of claim 1 wherein the polymers additionally have units from one or more comonomers, each selected from the group consisting of hydroxymethylmethacrylamide, hydroxymethylacrylamide, methyl methacrylate, other lower alkyl methacrylates, lower alkyl acrylates, acrylamide and methacrylamide.

12. The polymer composition of claim 1 wherein $R_3$ is a quaternary ammonium group having an associated anion selected from the group consisting of hydrochloric acid, sulfuric acid, phosphoric acid, sulfamic acid, acetic acid, citric acid, lactic acid, tartaric acid, malonic acid, benzenesulfonic acid, p-toluenesulfonic acid, cyclohexylsulfamic acid and quinic acid.

13. The composition of claim 1 wherein "a" is 0 to about 5; $R_1$ is hydrogen or lower alkyl, $R_2$ is hydrogen or lower alkyl, the linking group between the nitrogen atom of $R_3$ and the oxygen or nitrogen heteroatom of "A" or the nitrogen atom of the amide group is a straight chain alkylene group containing 1 to about 8 carbon atoms, and $R_3$ is a tertiary amine substituted with lower alkyl groups or a quaternary ammonium group substituted with lower alkyl groups; where "a" is not 0, "A" is oxyalkyl and "b" is 1 to about 5, or "A" is aminoalkyl, and "d" is 1 to about 5, and $R_4$ or $R_6$ is hydrogen; and wherein the composition is water soluble or a colloidal dispersion and the polymers have from 0 to about 0.05 percent crosslinking.

14. The composition of claim 13 wherein "a" is 0 or 1; $R_1$ is hydrogen or methyl, $R_2$ is hydrogen or methyl, the linking group between the nitrogen atom of $R_3$ and the nitrogen atom of "A" or the nitrogen atom of the amide group is a straight chain alkylene group containing 3 to about 5 carbon atoms, and $R_3$ is a tertiary amine group substituted with two methyl groups; where "a" is 1, "A" is aminoalkyl and "d" is 1 to about 5 and $R_6$ is hydrogen; and wherein the composition is water soluble and the polymers have a molecular weight mode of at least about 250,000 daltons and have from 0 to about 0.05 percent crosslinking.

15. The composition of claim 1 wherein the polymers are selected from the group consisting of:

poly(aminomethylacrylamide);

poly(aminomethylmethacrylamide); poly(methylaminomethylacrylamide);
poly(methylaminomethylmethacrylamide);
poly(dimethylaminomethylacrylamide);
poly(dimethylaminomethylmethacrylamide);
poly(aminoethylacrylamide);
poly(aminoethylmethacrylamide); poly(methylaminoethylacrylamide);
poly(methylaminoethylmethacrylamide);
poly(dimethylaminoethylacrylamide);
poly(dimethylaminoethylmethacrylamide);
poly(aminopropylacrylamide);
poly(aminopropylmethacrylamide); poly(methylaminopropylacrylamide);
poly(methylaminopropylmethacrylamide);
poly(dimethylaminopropylacrylamide);
poly(dimethylaminopropylmethacrylamide);
poly(aminobutylacrylamide);
poly(methylaminobutylacrylamide);
poly(dimethylaminobutylacrylamide);
poly(aminobutylmethacrylamide);
poly(methylaminobutylmethacrylamide);
poly(dimethylaminobutylmethacrylamide);
poly(aminopentylacrylamide);
poly(methylaminopentylacrylamide);
poly(dimethylaminopentylacrylamide);
poly(aminopentylmethacrylamide);
poly(methylaminopentylmethacrylamide);
poly(dimethylaminopentylmethacrylamide);
poly((dimethylaminopropylmethacrylamide)-co-(acrylamide));
poly((dimethylaminopropylmethacrylamide)-co-(methacrylamide));
poly(1-amino-3,6-diazaheptylacrylamide); and
poly(1-amino-3,6-diazaheptylmethacrylamide).

16. The composition of claim 1 wherein one or more of the polymers contain dimethylaminopropylmethacrylamide repeating units.

17. The composition of claim 1 wherein the polymers are homopolymers of dimethylaminopropylmethacrylamide.

18. The composition of claim 1 wherein one or more of the polymers contain dimethylaminopropylacrylamide repeating units.

19. The composition of claim 1 wherein the polymers are homopolymers of dimethylaminopropylacrylamide.

20. The composition of claim 1 wherein "a" is an integer between 0 and 10; "b", "c" and "d" are independently integers between 1 and 10; $R_3$ is a tertiary amino group; and the linking group is an alkylene group having 1 to 6 carbon atoms.

21. The composition of claim 1 wherein "a" is an integer between 0 and 10; "b", "c" and "d" are independently integers between 1 and 10; $R_3$ is a quaternary ammonium group; and the linking group is an alkylene group having 1 to 6 carbon atoms.

22. A composition for reducing the concentration of cholesterol in the blood of a host comprising a therapeutically effective amount of the composition of claim 1.

23. A pharmaceutical composition comprising a therapeutically effective amount of the composition of claim 1 and a pharmaceutically acceptable carrier.

24. A pharmacologically acceptable composition for the reduction of blood serum cholesterol in a host which comprises as an active ingredient a homopolymer of dimethylaminopropylmethacrylamide having (1) a molecular weight mode of at least about 250,000 daltons, (2) less than about 5 weight percent of the homopolymer having a molecular weight of about 50,000 or less and (3) no more than about 1000 parts unreacted dimethylaminopropylmethacrylamide monomer per million parts of polymer.

25. A pharmacologically acceptable composition for the reduction of blood serum cholesterol in a host which comprises as an active ingredient a homopolymer of dimethylaminopropylacrylamide having (1) a molecular weight mode of at least about 250,000 daltons, (2) less than about 5 weight percent of the homopolymer having a molecular weight of about 50,000 or less, and (3) no more than about 1000 parts unreacted dimethylaminopropylacrylamide monomer per million parts of polymer.

26. A composition for reducing the concentration of cholesterol in the blood of a host comprising
(a) a material which inhibits the biosynthesis of cholesterol in the liver of the host and
(b) polymers having units of the structure

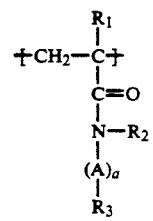

wherein
A is an aminoalkyl group —$(CHR_6)_d$—$NR_7$—, the alkyl being attached to the amide nitrogen;
a is an integer between 0 and about 10;
d is independently integers between 1 and about 10 ;
$R_1$ is hydrogen or a $C_1$-$C_8$ hydrocarbon group,
$R_2$, $R_6$ and $R_7$ are independently hydrogen, hydrocarbon groups or heteroatom-containing hydrocarbon groups; and

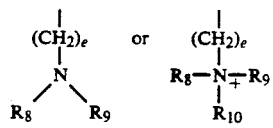

$R_3$ is
e is an integer from 1 to 6, and
$R_8$, $R_9$ and $R_{10}$ are independently hydrogen, hydrocarbon groups or heteroatom-containing hydrocarbon groups,
the composition being nontoxic and the polymers having a molecular size distribution with a mode of about 80,000 daltons or greater and from 0 to about 0.5 percent crosslinking.

27. The composition of claim 26 wherein the material is effective in inhibiting the biosynthesis by inhibiting HMG coenzyme A reductase.

28. The composition of claim 27 wherein the material is selected from the group consisting of lovastatin, simvastatin and pravastatin.

29. The composition of claim 28 wherein the material is lovastatin.

30. A method for reducing the blood cholesterol concentration in a host which comprises administering to the host an effective amount of a pharmacologically acceptable composition containing polymers having units of the structure

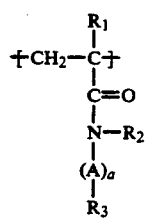

wherein

A is an aminoalkyl group $-(CHR_6)_d-NR_7-$, the alkyl being attached to the amide nitrogen;

a is an integer between 0 and about 10;

d is independently integers between 1 and about 10;

$R_1$ is hydrogen or a $C_1-C_8$ hydrocarbon group, $R_2$, $R_6$ and $R_7$ are independently hydrogen, hydrocarbon groups or heteroatom-containing hydrocarbon groups; and $R_3$ is

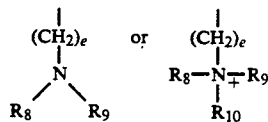

e is an integer from 1 to 6, and $R_8$, $R_9$ and $R_{10}$ are independently hydrogen, hydrocarbon groups or heteroatom-containing hydrocarbon groups, the composition being nontoxic and the polymers having a molecular size distribution with a mode of about 80,000 daltons or greater and from 0 to about 0.5 percent crosslinking.

31. The method of claim 30 wherein the amount administered is from about 2 to about 125 milligrams per kilogram of body weight per day.

32. The method of claim 30 wherein the amount administered is from about 35 to about 50 milligrams per kilogram of body weight per day.

33. The method of claim 30 wherein the administration is by ingestion.

34. The method of claim 33 wherein the host is a human being.

35. The method of claim 34 wherein the amount ingested is from about 0.2 to about 10 grams per day of the composition.

36. The method of claim 34 wherein the amount ingested is from about 3 to about 4 grams per day of the composition.

37. The method of claim 34 wherein the method further comprises administering a material which inhibits the biosynthesis of cholesterol in the liver of the host.

38. The method of claim 37 wherein the amount ingested is from about 1 to about 4.5 grams per day of the composition.

39. The method of claim 37 wherein the amount ingested is from about 1.5 to about 2 grams per day of the composition.

40. The method of claim 37 wherein the material is effective in inhibiting the biosynthesis by inhibiting HMG coenzyme A reductase.

41. The method of claim 40 wherein the material is selected from the group consisting of lovastatin, simvastatin and pravastatin.

42. The method of claim 41 wherein the material is lovastatin.

43. The method of claim 34 wherein the active ingredient of the composition comprises a polymer selected from the group consisting of:

poly(aminomethylacrylamide);
poly(aminomethylmethacrylamide); poly(methylaminomethacrylamide);
poly(methylaminomethylmethacrylamide);
poly(dimethylaminomethylacrylamide);
poly(dimethylaminomethylmethacrylamide);
poly(aminoethylacrylamide);
poly(aminoethylmethacrylamide); poly(methylaminoethylacrylamide);
poly(methylaminoethylmethacrylamide);
poly(dimethylaminoethylacrylamide);
poly(dimethylaminoethylmethacrylamide);
poly(aminopropylacrylamide);
poly(aminopropylmethacrylamide); poly(methylaminopropylacrylamide);
poly(methylaminopropylmethacrylamide);
poly(dimethylaminopropylacrylamide);
poly(dimethylaminopropylmethacrylamide);
poly(aminobutylacrylamide);
poly(methylaminobutylacrylamide);
poly(dimethylaminobutylacrylamide);
poly(aminobutylmethacrylamide);
poly(methylaminobutylmethacrylamide);
poly(dimethylaminobutylmethacrylamide);
poly(aminopentylacrylamide);
poly(methylaminopentylacrylamide);
poly(dimethylaminopentylacrylamide);
poly(aminopentylmethacrylamide);
poly(methylaminopentylmethacrylamide);
poly(dimethylaminopentylmethacrylamide);
poly((dimethylaminopropylmethacrylamide)-co-(acrylamide));
poly((dimethylaminopropylmethacrylamide)-co-(methacrylamide));
poly(1-amino-3,6-diazaheptylacrylamide); and
poly(1-amino-3,6-diazaheptylmethacrylamide).

44. The method of claim 30 wherein the active ingredient of the composition comprises a homopolymer of dimethylaminopropylmethacrylamide.

45. The method of claim 30 wherein the active ingredient of the composition comprises a homopolymer of dimethylaminopropylacrylamide.

* * * * *